US005807895A

United States Patent [19]
Stratton et al.

[11] Patent Number: 5,807,895
[45] Date of Patent: Sep. 15, 1998

[54] USE OF PROSTAGLANDIN E1, E2 OR ANALOGS TO PREVENT RENAL FAILURE INDUCED BY MEDICAL TESTS THAT UTILIZE CONTRAST MEDIA AGENTS

[75] Inventors: Henry T. Stratton, Glendale; Tammy K. Antonucci, Mequon, both of Wis.; Erwin Schollmayer, Leverkusen, Germany

[73] Assignee: Schwarz Pharma, Inc., Mequon, Wis.

[21] Appl. No.: 563,392

[22] Filed: Nov. 28, 1995

Related U.S. Application Data

[63] Continuation-in-part of Ser. No. 346,374, Nov. 29, 1994, abandoned.

[51] Int. Cl.$^6$ .................................................. A61K 31/557
[52] U.S. Cl. ............................................................ 514/573
[58] Field of Search ............................................... 514/573

[56] References Cited

U.S. PATENT DOCUMENTS

| | | | |
|---|---|---|---|
| 3,636,120 | 1/1972 | Pike | 260/586 R |
| 3,828,106 | 8/1974 | Rudel | 424/239 |
| 3,833,640 | 9/1974 | Pike | 260/468 |
| 3,914,282 | 10/1975 | Pike | 260/468 D |
| 3,922,297 | 11/1975 | Pike | 260/468 D |
| 3,969,376 | 7/1976 | Magerlein | 260/408 |
| 3,984,455 | 10/1976 | Beal, III et al. | 260/468 D |
| 4,054,736 | 10/1977 | Hayashi et al. | 536/103 |
| 4,097,516 | 6/1978 | Buckler | 260/465 F |
| 4,103,026 | 7/1978 | Carlson | 424/305 |

FOREIGN PATENT DOCUMENTS 0 407 148 A2
 (AA) 9/1991 European Pat. Off. .

OTHER PUBLICATIONS

Wiegmann, "Contrast Nephrotoxicity: The Role of Prostaglandins and Effect of Misorprostol Treatment", National Technical Information Service database, 1992.

L. Gurkowski et al., "Prevention of Contrast Induced Renal Dysfunction by Misoprostil: Results of a Prospective, Randomized, Double–Blind Study", Journal of American Society of Nephrology, vol. 5, No. 3, Sep. 1994.

L. Gurkowski et al., "Misoprostil Prevents Reductions in Renal Blood Flow After Radio–Contrast Infusion During Prostaglandin Inhibition with Indomethacin", Journal of American Society of Nephrology, vol. 5, No. 3, Sep. 1994.

Eur. J. Nucl. Med., vol. 14, No. 5–6, 1988, p. 297, XP000569763, Z. Szabo et al., "Investigation of the Renal Protective Effects of Prostaglandine E 1 (PGE1) in Experimental Ischemia: Measurement of Renal Function with Tc . . . ", see abstract.

Eur. J. Vasc. Surg., vol. 3, No. 1, Feb. 1989, pp. 5–13, XP000569756, G. Torsello et al., "Effects of Prostaglandin E1 (PGE1) on Experimental Renal Ischaemia", see abstract.

Fukushima J. Med. Sci., vol. 39, No. 2, Dec. 1993, pp. 117–119, XP000569761, Y. Matsumoto et al., "Systematic Mangement of Graft–Versus–Host Disease (GVHD)" see abstract.

Invest. Radiol., vol. 10, No. 4, 1975, pp. 284–299, XP000569755, P. S. Moskowitz et al., "Diuresis and Improved Renal Hemodynamics Produced by Prostaglandin E1 in the Dog with Norepinephrine–Induced Acute Renal Failure" see p. 298.

Prostaglandins Leukotrienes Med., vol. 9, No. 1, 1982, pp. 85–107, XP000569781, A. K. Mandal et al., "The Spleen and Acute Renal Failure: Mechanisms of Renal Protection by Splenectomy. Involvement of Prostaglandins", see abstract.

Am. J. Cardiol., vol. 66, No. 14, 1990, pp. 18F–22F, XP000569719, G. A. Porter, "Experimental Contrast–Associated Nephropathy and Its Clinical Implications", see abstract.

Invest. Radiol., vol. 23, No. Suppl. 1, Sep. 1988, pp. s178–s181, XP000569760, Z. Parvez et al., "Effect of Contrast Media on Prostaglandin Synthesis In Vivo" see abstract.

Solomon et al., *Effects of Saline, Mannitol, and Furosemide on Acute Decreases in Renal Function Induced by Radiocontrast Agents,* The New England Journal of Medicine, vol. 331, No. 21, 1416–1420 (1994).

*Textbook of Internal Medicine,* published by J.B. Lippincott Company, Philadelphia, 2d Edition, vol. 1, p. 817 (1992).

Weisberg et al., *Risk of Radiocontrast Nephropathy in Patients With and Without Diabetes Mellitus,* Kidney International, vol. 45, 259–265 (1994).

Olivero, *Postsurgical Acute Renal Failure: Which Patients are at Greatest Risk?,* Journal of Critical Illness, vol. 9, No. 7, 673–685 (Jul. 1994).

Cantley et al., *Role of Endothelin and Prostaglandins in Radiocontrast–Induced Renal Artery Constriction,* Kidney International, vol. 44, 1217–1223 (1993).

Abe et al., *The Effect of Prostaglandin $E_1$ During Cardiopulmonary Bypass on Renal Function After Cardiac Surgery,* Europe Journal of Clinical Pharmacology, vol. 45, 217–220 (1993).

Pollack et al., *A Trial of the Prostaglandin $E_1$ Analogue, Enisoprost, to Reverse Chronic Cyclosporine–Associated Renaly Dysfunction,* American Journal of Kidney Diseases, vol. XX, No. 4, 336–341 (1992).

(List continued on next page.)

*Primary Examiner*—C. Warren Ivy
*Assistant Examiner*—Evelyn Huang
*Attorney, Agent, or Firm*—Merchant, Gould, Smith, Edell, Welter & Schmidt, P.A.

[57] ABSTRACT

A method of preventing renal failure or dysfunction caused by medical tests which utilize contrast media by administering, preferably by intravenous infusion or injection, a prostaglandin selected from $PGE_1$, $PGE_2$, $PGI_2$ or an analog or pharmaceutically acceptable salt thereof and preferably in a form of a complex with α-cyclodextrin, to a patient at risk, for example, a diabetic.

11 Claims, 3 Drawing Sheets

OTHER PUBLICATIONS

Moran et al., *Prevention of Acute Graft Rejection by the Prostaglandin $E_1$ Analogue Misoprostol in Renal–Transplant Recipients treated with Cyclosporine,* The New England Journal of Medicine, vol. 332, No. 17, 1183–1188 (1990).

Broggi et al., *Systemic Administration of the PGE–1 Analogue Alprostadil for Prophylaxis of Early Kidney Graft Failure,* Transplantation Proceedings, vol. 21, No. 1, 1546–1547 (1989).

Ninomeya et al., *Renal Effects of Prostaglandin $E_1$ Type 2 (Non–Insulin–Dependent) Diabetic Patients with Subclinical Nephropathy,* Diabetes Research, vol. 10, 129–134 (1985).

Niwa et al., *Beneficial Effects of Prostaglandin $E_1$ in Rapidly Progressive Clomerulonephritis,* The New England Journal of Medicine, vol. 308, No. 16, p. 969 (Apr. 21, 1983).

Niwa et al., *Improvement of Renal Function with Prostaglandin $E_1$ Infusion in Patients with Chronic Renal Disease,* The Lancet, p. 687 (Mar. 20, 1982).

*Goodman & Gilman's: "The Pharmacological Basis of Therapeutics",* Eight Edition, Chapter 24, 600–611 (1990).

USE OF PROSTAGLANDIN E1, E2 OR ANALOGS TO PREVENT RENAL FAILURE INDUCED BY MEDICAL TESTS THAT UTILIZE CONTRAST MEDIA AGENTS

This application is a continuation-in-part of U.S. application Ser. No. 08/346,374, filed Nov. 29, 1994 abandoned.

FIELD OF THE INVENTION

This application is directed to the use of $PGE_1$, $PGE_2$, $PGI_2$ or analogs of those compounds for prevention of renal failure or dysfunction induced by medical tests which utilize contrast media.

BACKGROUND OF THE INVENTION

The naturally occurring prostaglandins are comprised of several biological entities including PGD, PGE, PGF, PGG, PGH and PGI. It has been well documented that prostaglandins have effects on many of the organs and systems of the body. One of the systems affected by prostaglandins is the cardiovascular system, finding therapeutic use in treating peripheral arterial occlusive disease, erectile dysfunction, congenital heart defects in newborns, congestive heart failure, pulmonary hypertension and vasoconstriction. Prostaglandins have also been used for their effects on cerebral ischemia and for maintenance of cerebral blood flow and $C_2$ reactivity during surgery to repair cerebral aneurysms; in modulating the inflammatory response; to inhibit gastric acid secretion stimulated by feeding or cystamine or gastrin; to protect gastric mucosa and to relax the circular muscle along the gastrointestinal tract.

In the kidney, the prostaglandins modulate renal blood flow and may serve to regulate urine formation by both renovascular and tubular effects. In clinical studies, $PGE_1$ has been used to improve creatinine clearance in patients with chronic renal disease, to prevent graft rejection and cyclosporine toxicity in renal transplant patients, to reduce the urinary albumin excretion rate and N-acetyl-beta-D-glucosaminidase levels in patients with diabetic nephropathy, and to improve urea clearance in healthy volunteers. $PGE_1$ also has been administered intravenously during surgeries to prevent renal failure.

Renal dysfunction and/or renal failure is manifested in the body in a number of different ways. Any one or a combination of the following manifestations could indicate renal dysfunction or failure in a patient: lower than normal creatinine clearance; lower than normal free water clearance; higher than normal blood urea and/or nitrogen and/or potassium and/or creatinine levels; altered activity of kidney enzymes such as gamma glutamyl synthetase, alanine phosphatidase, N-acetyl-beta-D-glucosaminidase, or beta-2-microglobulin; altered urine osmolarity or volume; increase over normal levels or new observation of microalbuminuria or macroalbuminuria; or need for dialysis. Successful prevention of renal dysfunction or renal failure is indicated if the above described events do not occur at all, if they occur with less severity, if they occur in fewer patients at risk for renal dysfunction or renal failure; or if the patient recovers from these problems more quickly than normal.

Acute renal failure caused by the injection of contrast media has been recognized for many years as a complication of procedures utilizing such media. It has been estimated that the incidence of acute renal failure directly induced by contrast media is 10–15%, while the incidence of contrast associated nephropathy defined by clinically significant increases in serum creatinine is as high as 22%. See Porter, Am. J. Cardiol., 64:22E–26E (1989). The peak creatinine concentration occurs within 5 days of exposure to the contrast media and usually resolves satisfactorily, but in up to 10% of at risk patients, dialysis is required. Two of the leading risk factors for contrast associated nephropathy are pre-existing renal insufficiency, which increases the risk for developing contrast associated nephropathy 6 to 10 fold, and diabetes mellitus. When both conditions co-exist, the incidence of contrast associated nephropathy approaches 100%.

The pathogenesis of radiocontrast-induced nephropathy (RCN) is still poorly understood. Several mechanisms have been proposed for RCN including direct tubule toxicity, an imbalance between perfusion and metabolic demands, intraluminal obstruction and immunological injury.

Direct tubule toxicity has been suggested by studies demonstrating increased proteinuria and enzymuria (Ludwin and Luxton, in Solez et al. Acute Renal Failure: Diagnosis, Treatment & Prevention, pp. 139–147, (1991)). Histological assessment often reveals 'vacuolation' of proximal tubule epithelium, although it has recently been shown that this is in fact due to uptake of contrast medium into lysosomes—the functional significance of which is unknown (Powell et al., Eur. Radiol. 5, pp. 176∝180 (1995)). Other potential mechanisms invoked include systemic and/or intrarenal haemodynamic changes, intraluminal obstruction and immunological injury. Another recent mechanism that has been proposed in some studies (Agmon et al., J. Clin. Invest. 94, pp. 1069–75 (1994); Brezis et al., J. Clin. Invest. 88, pp. 390–5 (1991); Heyman et al., J. Clin. Invest. 82, pp. 401–12 (1988); Heyman et al., Kidney Int. 40, pp. 632–42 (1991)) is that experimental radiocontrast nephropathy may result from regional hypoxia in the outer medulla, with selective necrosis of the medullary thick ascending limbs of the loop of Henle (Agmon et al.; Brezis et al; Heyman et al., 1988; Heyman et al., 1991). This relative deficit in oxygen delivery may be further augmented by an increase in oxygen demand from resorption of hypertonic media in the thick ascending limb; however, iso-osmolar contrast media have also been shown to cause nephrotoxicity and therefore the putative increase in metabolic workload is not the sole factor.

It has been shown that endothelin, a potent vasoconstrictor, is released following radiocontrast administration (Heyman et al., J. Am. Soc. Nephrol. 3, pp. 58–65 (1992)). But, in direct opposition to that observation, it also has been shown that $PGE_2$, a potent vasodilator, is released following radiocontrast administration (Cantley et al., Kidney Int. 44, pp. 1217–23 (1993)). With these two seemingly conflicting observations, it is difficult to postulate a cogent argument relative to ischemia, vasodilation and/or vasoconstriction for the mechanism of contrast-induced nephrotoxicity. However, it has been clearly demonstrated in many studies (Weisberg et al., Kidney International, Vol. 45, pp. 259–265 (1994); Solomon, American Society of Nephrology Short Course, J. Am. Soc. Nephrology, Vol. 6 (1995); Fuchs et al., J. Am Soc. Nephrology, Vol. 6, p. 997 (1995)) that administration of vasodilating drugs such as mannitol, dopamine, furosemides, insulin-like growth factor and atrial natriuretic peptide does not prevent RCN from occurring. In fact, in diabetics it has been shown that such drugs actually worsen the level of renal dysfunction.

SUMMARY OF THE INVENTION

We have discovered that $PGE_1$, $PGE_2$, $PGI_2$, or their analogs in any of the known chemical formulations may be used prophylactically for the prevention of renal failure or dysfunction induced by medical tests that use contrast media. The risk of acute renal failure after contrast utilizing procedures is documented, especially in populations at risk such as the elderly, diabetics, patients with cardiac insufficiency or impaired renal function and patients currently taking diuretics or non-steroidal anti-inflammatory drugs. We conceived that external administration of prostaglandins or their analogs during and/or immediately after radiocontrast procedures can prevent renal failure or dysfunction.

DETAILED DESCRIPTION OF THE INVENTION

Figure 1:
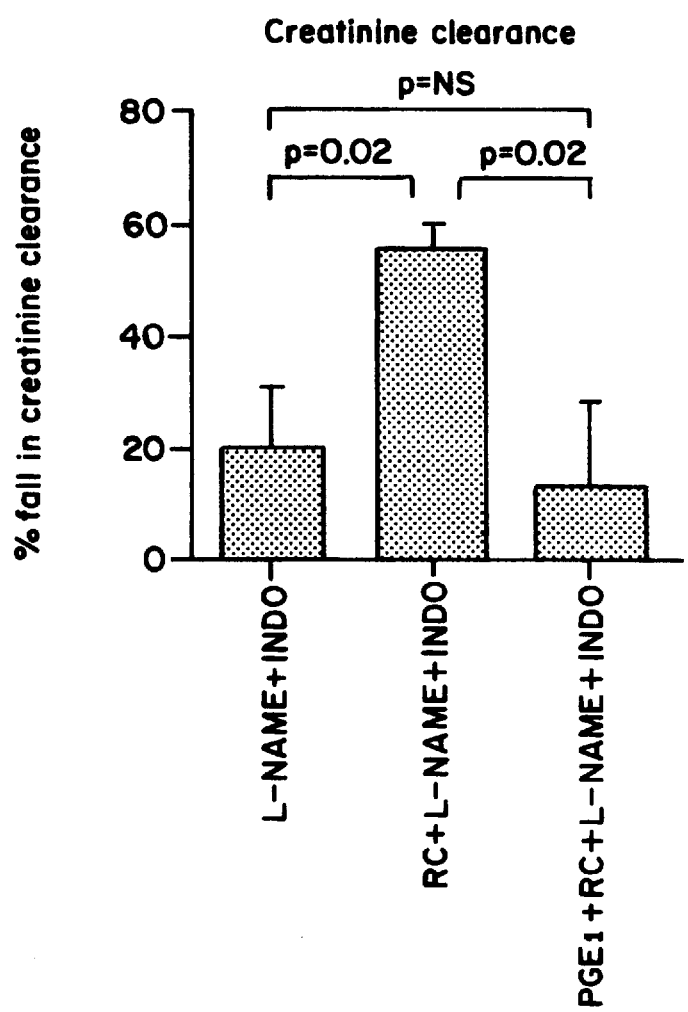
FIG. 1 is a graphical depiction of the percentage fall in creatinine clearance following experimental intervention.

There are a great many contrast agents in use today in connection with medical tests such as, for example, x-rays, angiography, CT scans, and so on. Agents that enter systemic circulation must be eliminated via the kidneys, and it is at this point that the nephrotoxicity of the contrast agents can result in acute renal failure. Contrast media induced acute renal failure appears to develop from the combined effects of contrast induced renal vasoconstriction with resulting ischemia, direct tubular cell toxicity, and intratubular precipitation of the contrast agent with proteins and membrane fragments which results in intratubular constriction. See the *Textbook of Internal Medicine*, J. B. Lippincott Company, p.817.

Some of the commonly used contrast media whose use may raise concerns about contrast media induced renal failure include meglumine diatrizoate; sodium diatrizoate; iocetamic acid; meglumine iodipamide; meglumine iodamide; meglumine and sodium iothalamate; meglumine and sodium ioxaglate; and metrizamide and sodium trypanoate. Many other contrast media are known in the art and may be found in references such as Skucas, *Radiographic Contrast Agents*, 2d.Ed., Aspen Publishers Inc. (1989). The method of the instant invention is not dependent on the nature of the contrast media employed, however, and can be used to prevent renal failure or dysfunction induced by the use of any contrast media.

The phrases "$PGE_1$, $PGE_2$, $PGI_2$ or an analog thereof" and "prostaglandin compound(s) or analog(s)" include the naturally occurring prostaglandins and any of their known derivatives, including their metabolites, stereoisomers and pharmaceutically acceptable salts. $PGE_1$, $PGE_2$, and $PGI_2$ are well known compounds and can be synthesized by methods known in the art. See, e.g., Goodman and Gilman, *The Pharmacological Basis of Therapeutics*, Eighth Ed., Pergamon Press, pp.601–604 (1990). Some derivatives of the naturally occurring prostaglandins within the scope of the invention can be found in U.S. Pat. Nos. 3,833,640; 3,914,282; 3,922,297; 3,969,376; 3,984,455; 4,097,516; and 4,103,026, all of which are incorporated herein by reference.

In the method of the invention, the prostaglandin compounds or their analogs may be used in any of their known formulations. Preferably the compounds are administered intravenously or by injection. Compositions to be administered intravenously or by injection can be prepared as solutions of the prostaglandin compound or derivative in, for example, an isotonic aqueous solution, an alcohol solution, an ethanol-saline solution, or an ethanol-dextrose solution. If an aqueous isotonic solution is prepared, the acid and salt forms of the prostaglandin compounds or derivatives are especially suitable. The pharmaceutically acceptable salt can be, for example, an alkali metal salt such as sodium or potassium, an alkali earth metal salt such as calcium or magnesium, an ammonium salt or a pharmaceutically acceptable amine salt such as methylamine, diethylamine, monoethanolamine, diethanolamine, lysine, and so on. Ethanol can be added to the solution to increase solubility and other additives such as methylparaben or other ingredients such as fillers, colorings, flavorings, diluents and the like can be included. The compositions can also be administered as a suspension of the acid, salt or ester form of the prostaglandin compound or analog in aqueous or non-aqueous media.

Among the preferred prostaglandin formulations are complexes of the active ingredient with α-cyclodextrin. Preparation of complexes of prostaglandin compounds and analogs with α-cyclodextrin clathrates are described in detail in Hayashi et al., U.S. Pat. No. 4,054,736 which is incorporated herein by reference. Complexes wherein the ratio of α-cyclodextrin:prostaglandin is 97:3 are especially preferred.

The prostaglandins can also be administered orally in solid solution with lipids such as cholesterol acetate. The inclusion of lipid in the formulation markedly increases absorption of the prostaglandin compound or analog. Preparation of such formulations is described in detail in Rudel, U.S. Pat. No. 3,828,106, which is incorporated herein by reference.

In the method of the invention, the prostaglandin compounds or analogs may be administered to any patient in need of a medical procedure using a systemic contrast medium. The risk of contrast media induced renal failure increases as the amount of contrast media used increases, and so administration of prostaglandin compounds or analogs to prevent such renal failure is particularly recommended for patients who need an intravasal contrast procedure using at least 30 ml of a contrast medium. The risk of contrast media induced acute renal failure is higher in groups such as the elderly, diabetics, persons with cardiac insufficiency, patients taking diuretics or nonsteroidal anti-inflammatory drugs, patients with impaired renal function (measured by serum creatinine levels above normal ranges), or patients who have had contrast media injections within 72 hours of the current procedure. Patients falling into any of these categories in particular, therefore, should benefit from the administration of prostaglandin compounds or analogs to prevent contrast media induced acute renal failure.

While the prostaglandin compounds or analogs may be administered to the patients in any of the known formulations or modes of administration, they are preferably administered by intravenous infusion or injection.

Dosages of the compounds administered can range from about 5 to about 60/ng/min/kg body weight, with the preferred dosage range being from about 10 ng/kg/min to about 30 ng/kg/min. If the dose is administered by intravenous injection, it should not exceed about 100 µg/kg body weight per day. The prostaglandin compounds or analogs may be administered immediately before, during, and immediately after the procedure which utilizes contrast media. If the prostaglandin compounds or analogs are administered by infusion, the dose is preferably given up to 1 hour before the procedure which utilizes contrast media, continued throughout the procedure and after the procedure for at least 1 hour but not more than 12 hours. Most preferred is continuous administration over a 6 hour period beginning 1 hour before the procedure using contrast media. If the prostaglandin compounds or analogs are administered by injection, then the dose should be given up to 1 hour prior to and/or during the procedure which utilizes contrast media.

The following are non-limiting examples of the use of prostaglandin compounds for the prevention of contrast media induced acute renal failure or dysfunction.

Example 1

A concentrated aqueous solution of a complex of $PGE_1$, and α-cyclodextrin is prepared for continuous intravenous infusion by infusion pump. The $PGE_1$, complex is administered to a patient suffering from insulin-dependent diabetes mellitus in need of an intravasal radiocontrast procedure with at least 30 ml of a radiocontrast medium. Administration of the compound by infusion pump begins 1 hour before the application of the radiocontrast medium and continues for 6 hours at a dosage of 30 ng/kg/min. Serum creatinine and creatinine clearance are monitored to determine renal function and the absence of contrast media induced renal dysfunction.

Example 2

The procedure of Example 1 is repeated, with a dosage of $PGE_1$ of 10 ng/kg/min over 6 hours.

Example 3

The $PGE_1$, complex of Example 1 is administered to a patient in need of an intravasal radiocontrast procedure with at least 30 ml of a radiocontrast medium who has serum creatinine levels above normal ranges. Administration of the compound by infusion pump begins 1 hour before the application of the radiocontrast medium and continues for 6 hours at a dosage of 30 ng/kg/min. Serum creatinine and creatinine clearance are monitored to determine renal function and the absence of contrast media induced renal failure.

Example 4

The procedure of Example 3 is repeated, with a dosage of $PGE_1$ of 10 ng/kg/min over 6 hours.

Example 5

The $PGE_1$, complex of Example 1 is administered to a patient in need of an intravasal radiocontrast procedure with at least 30 ml of a radiocontrast medium who has had a prior radiocontrast procedure within 72 hours of the current procedure. Administration of the compound by infusion pump begins 1 hour before the application of the radiocontrast medium and continues for 6 hours at a dosage of 30 ng/kg/min. Serum creatinine and creatinine clearance are monitored to determine renal function and the absence of contrast media induced renal dysfunction.

Example 6

The procedure of Example 5 is repeated, with a dosage of $PGE_1$ of 10 ng/kg/min over 6 hours.

Example 7

To further demonstrate the method of the invention, the effect of administration of $PGE_1$ to rats prepared in the manner described by Agmon et al., *J. Clin. Invest.* 94, pp. 1069–75 (1994), subject to injection with radiocontrast agents was investigated.

Adult male Wistar rats (200–302 g body weight) were used. On day 1, rats were placed in metabolism cages overnight for estimation of creatinine clearance. On day 2, animals were anaesthetized with Hyporm (fentanyl citrate and fluanisone, 0.16 ml i.m.) and Diazepam (0.25 mg i.p.) and placed under a warming lamp. A 0.5 ml sample of blood was withdrawn by tail vein puncture, and two 25 gauge butterfly needles were sited in the lateral tail veins for administration of drugs. Thirty minutes prior to radiocontrast agent injection, indomethacin (10 mg/kg) was administered intravenously (i.v.), followed 15 minutes later by the nitric oxide synthase inhibitor N-nitro-L-arginine methyl ester (L-NAME, 10 mg/kg i.v.). After a further 15 minutes, the hyperosmolar, ionic radiocontrast agent sodium iothalamate 70% (Conray 420, 6 ml/kg) or NaCl 0.9% (6 ml/kg) was slowly injected i.v. over 3 minutes.

Immediately prior to indomethacin administration, an infusion of either NaCl 0.9% or $PGE_1$ (1 µg/kg/min, dissolved in NaCl 0.9%) was commenced at an infusion rate of 0.6 ml/hour and continued for 3 hours.

Rats were assigned to three groups:
(1) indomethacin with L-NAME, followed by saline (n=6 rats);
(2) indomethacin with L-NAME, followed by sodium iothalamate (n=11 rats); or
(3) infusion of $PGE_1$, in addition to indomethacin, L-NAME and sodium iothalamate (n=10 rats).

The rats were then returned to the metabolism cages and a further clearance study was performed overnight. On day 3, a further blood sample was obtained under terminal anaesthesia.

Results are expressed as means ± SEM (standard error means), and analyzed for significant variation using the Welch unpaired t-test. A p value of less than 0.05 was considered significant.

Inhibition of endothelium-derived vasodilation with a combination of intravenous L-NAME and indomethacin caused a degree of renal impairment with a percentage fall in creatinine clearance of 20±11% from pretreatment values. Addition of the radiocontrast agent sodium iothalamate greatly aggravated this decrease in renal function, with a fall in creatinine clearance of 56±4%. Co-administration of $PGE_1$, and the radiocontrast agent abolished the further decrease seen with the addition of a radiocontrast agent (FIG. 1).

Figure 2:
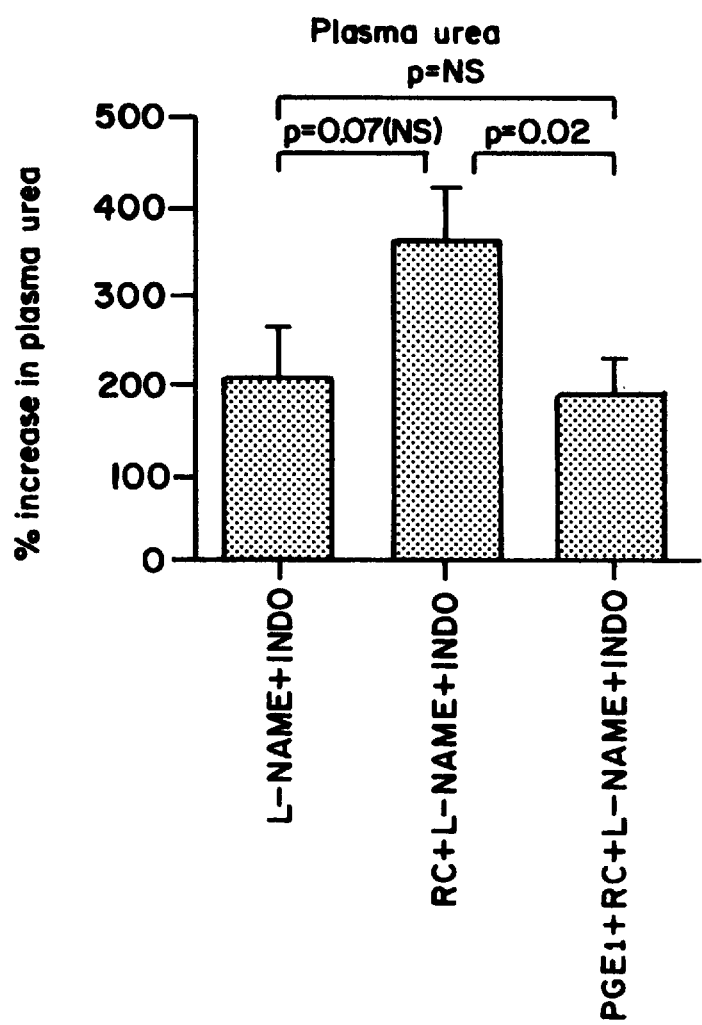
FIG. 2 depicts the percentage rise in plasma urea levels following experimental intervention.
Figure 3:
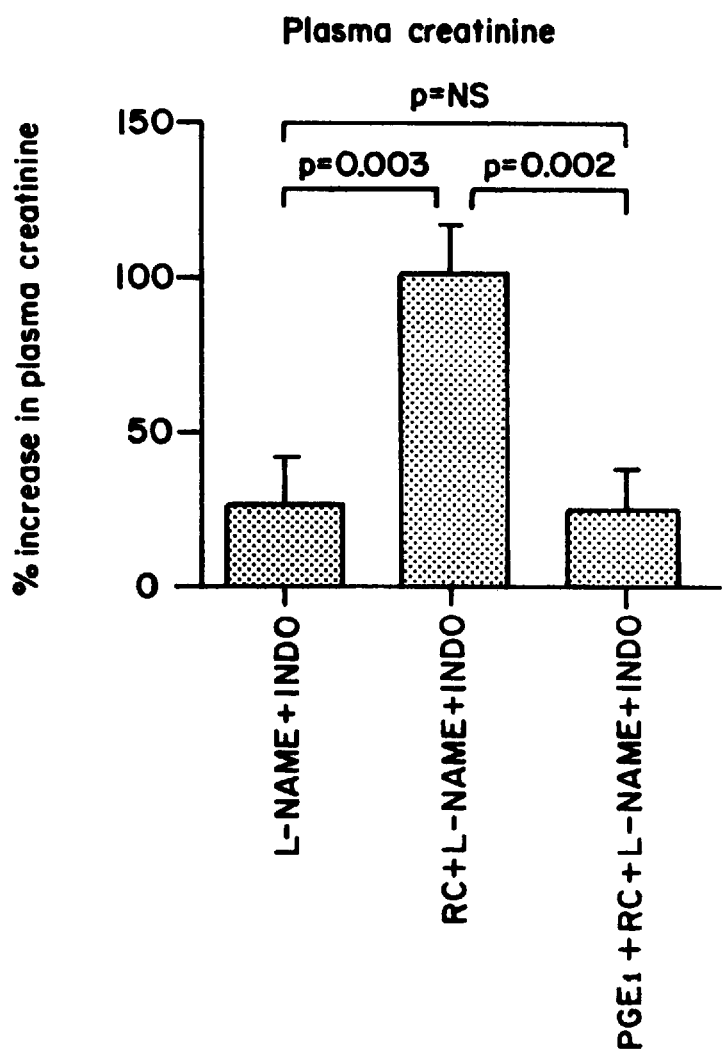
FIG. 3 depicts the percentage rise in plasma creatinine following experimental intervention.

Plasma urea levels rose by 211±52% in the animals that received L-NAME and indomethacin, and by 361±58% in animals that received the radiocontrast agent in addition to L-NAME and indomethacin. Treatment with $PGE_1$ limited the rise in plasma urea to 188±39% (FIG. 2). Plasma creatinine levels rose by 26±11 following administration of L-NAME and indomethacin. When the radiocontrast agent was also administered, however, it rose by 101±16%. Co-administration of $PGE_1$, again blocked this further rise (FIG. 3). All animals exhibited a rise in urinary protein excretion, and there were no significant differences in urinary flow rates between the various groups.

We claim:
1. A method of preventing renal dysfunction caused by medical procedures which utilize contrast media comprising administration by intravenous infusion of an effective amount of a prostaglandin compound selected from the group consisting of $PGE_1$, $PGE_2$ or pharmaceutically acceptable salt or ester thereof to a patient subject to such a procedure and at risk of renal dysfunction up to one hour before the procedure, continuing administration throughout the procedure and after the procedure for 1 to 12 hours.

2. A method according to claim 1 wherein an effective amount of $PGE_1$ or a pharmaceutically acceptable salt thereof is administered.

3. A method according to claim 2 wherein the $PGE_1$ is administered as a complex of $PGE_1$ and $\alpha$-cyclodextrin.

4. A method according to claim 1 wherein an effective amount of $PGE_2$ or a pharmaceutically acceptable salt thereof is administered.

5. A method according to claim 1 wherein the prostaglandin compound is administered to a patient who is suffering from diabetes mellitus.

6. A method according to claim 1 wherein the prostaglandin compound is administered in a dosage range of from about 5 to about 60 ng/min/kg body weight.

7. A method according to claim 6 wherein the prostaglandin compound is administered in a dosage range of from about 10 ng/kg/min to about 30 ng/kg/min.

8. A method according to claim 3 wherein the prostaglandin compound is administered to a patient who is diabetic.

9. A method according to claim 3 wherein the prostaglandin compound is administered in a dosage range of from about 5 to about 60 ng/min/kg body weight.

10. A method according to claim 9 wherein the prostaglandin compound is administered in a dosage range of from about 10 ng/kg/min to about 30 ng/kg/min.

11. The method of claim 1 wherein the prostaglandin compound is administered continuously for a six hour period beginning one hour before the procedure.

* * * * *

UNITED STATES PATENT AND TRADEMARK OFFICE
CERTIFICATE OF CORRECTION

PATENT NO. : 5,807,895

DATED : SEPTEMBER 15, 1998

INVENTOR(S) : STRATTON ET AL.

It is certified that error appears in the above-identified patent and that said Letters Patent is hereby corrected as shown below:

Col. 1, line 26: "$C_2$" should read --$CO_2$--

Col. 2, line 23: "176∝180" should read --176-180--

Col. 6, line 51: insert --%-- after "±11"

Signed and Sealed this

Ninth Day of November, 1999

Attest:

Q. TODD DICKINSON

*Attesting Officer*  *Acting Commissioner of Patents and Trademarks*